(12) United States Patent
Chen et al.

(10) Patent No.: US 10,351,536 B2
(45) Date of Patent: Jul. 16, 2019

(54) CRYSTALLINE FORMS OF LESINURAD AND ITS SODIUM SALT

(71) Applicants: CRYSTAL PHARMATECH CO., LTD., Suzhou (CN); SUZHOU PENGXU PHARMATECH CO., LTD., Suzhou (CN)

(72) Inventors: Minhua Chen, Scotch Plains, NJ (US); Yanfeng Zhang, Suzhou (CN); Chaohui Yang, Suzhou (CN); Xiaoyu Zhang, Suzhou (CN); Peng Wang, Forest Hills, NY (US); Pixu Li, Suzhou (CN)

(73) Assignees: Crystal Pharmatech Co., Ltd., Suzhou, Jiangsu (CN); Suzhou Pengxu Pharmatech Co., Ltd., Suzhou, Jiangsu (CN)

( * ) Notice: Subject to any disclaimer, the term of this patent is extended or adjusted under 35 U.S.C. 154(b) by 11 days.

(21) Appl. No.: 15/038,470

(22) PCT Filed: Nov. 20, 2014

(86) PCT No.: PCT/IB2014/003077
§ 371 (c)(1),
(2) Date: May 22, 2016

(87) PCT Pub. No.: WO2015/075561
PCT Pub. Date: May 28, 2015

(65) Prior Publication Data
US 2016/0297778 A1    Oct. 13, 2016

(30) Foreign Application Priority Data

Nov. 22, 2013 (CN) .......................... 2013 1 0597329
Dec. 2, 2013 (CN) .......................... 2013 1 0633354
Nov. 19, 2014 (CN) .......................... 2014 1 0659325
Nov. 19, 2014 (CN) .......................... 2014 1 0660068

(51) Int. Cl.
*C07D 249/12* (2006.01)

(52) U.S. Cl.
CPC ........ *C07D 249/12* (2013.01); *C07B 2200/13* (2013.01)

(58) Field of Classification Search
CPC .......................... C07D 249/12; C07B 2200/13
See application file for complete search history.

(56) References Cited

U.S. PATENT DOCUMENTS

2009/0197825 A1* 8/2009 Quart .................. C07D 249/12
514/46
2010/0056464 A1   3/2010 Gunic et al.

FOREIGN PATENT DOCUMENTS

WO      2011/085009 A2      7/2011
WO   WO 2011/085009    *    7/2011 ........... C07D 249/12
WO      2012/092395 A2      7/2012

OTHER PUBLICATIONS

Hurst et al., Analytica Chimica Acta, 337 (1997), 233-52.*
Campbell Roberts et al., J. Pharm. Biomed. Anal., 28 (2002) 1149-59.*
Chen et al., J. Pharm. Sci., (1999), v. 88, p. 1191-1200.*
Tiwari et al., J. Pharm. Biomed. Anal., 43 (2007) 865-72.*
Brittain (Polymorphism in Pharmaceutical Solids, vol. 95, 1999, Taylor & Francis, Harry G. Brittain (Ed.), 427 pp.).p. 1-219 provided.*
Morissette et al. (Advanced Drug Delivery Reviews 56 (2004) 275-300).*

* cited by examiner

*Primary Examiner* — Robert H Havlin
(74) *Attorney, Agent, or Firm* — VLP Law Group LLP; Kent H. Cheng

(57) ABSTRACT

Novel crystalline forms of lesinurad and its sodium salt, processes for their preparation, pharmaceutical compositions comprising these new forms, and use of them for treating or delaying progression or onset of diseases or disorders related to activity of uric acid transporter 1 (URAT1) proteins are disclosed. These novel forms were characterized by X-ray powder diffraction, differential scanning calorimetry, and other techniques. They can be readily prepared and are suitable for preparation of solid dosage forms owing to their ease of handling and superior pharmacological properties.

5 Claims, 11 Drawing Sheets

CRYSTALLINE FORMS OF LESINURAD AND ITS SODIUM SALT

CROSS REFERENCE TO RELATED APPLICATIONS

This application claims priority under 35 U.S.C. § 119(a) to Chinese Patent Application No. 201310597329.6, filed on Nov. 22, 2013; Application No. 201310633354.5, filed on Dec. 2, 2013; Application No. 201410659325.0, filed on Nov. 19, 2014; and Application No. 201410660068.2, filed on Nov. 19, 2014, all of which are herein incorporated by reference in their entireties.

FIELD OF THE INVENTION

This invention relates to novel crystalline forms of lesinurad and its sodium salt, and their pharmaceutical compositions, methods of preparation, and methods of uses.

BACKGROUND OF THE INVENTION

Hyperuricemia is characterized by higher than normal blood levels of uric acid, sustained over long periods of time, often due to enhanced uric acid production (e.g., 10-20%) and/or reduced renal excretion (e.g., 80-90%) of uric acid. Hyperuricemia may be caused by numerous factors, such as obesity/weight gain, excessive alcohol use, excessive dietary purine intake, and certain medications, including low-dose aspirin, diuretics, niacin, cyclosporine, some high blood pressure drugs, some cancer chemotherapeutics, immunosuppressive and cytotoxic agents, and so on. In certain instances, hyperuricemia may be asymptomatic, but it may be associated with the following conditions: gout, gouty arthritis, uric acid stones in the urinary tract (urolithiasis), deposits of uric acid in the soft tissue (tophi), deposits of uric acid in the kidneys (uric acid nephropathy), and impaired kidney function, possibly leading to chronic and acute renal failure. Defective uric acid processing may lead to elevated levels of uric acid in the blood causing recurring attacks of joint inflammation (arthritis), uric acid deposits in and around the joints, tophaceous gout, formation of tophi, decreased kidney function, and kidney stones. Approximately 3 to 5 million people in the United States suffer from attacks of gout. In certain instances, gout is one of the most common forms of arthritis, accounting for approximately 5% of all arthritis cases. In certain instances, kidney failure and urolithiasis occur in 10-18% of individuals with gout and are common sources of morbidity and mortality from the disease.

Lesinurad inhibits the uric acid transporter 1 (URAT1) protein, increasing uric acid excretion and thereby lowering serum uric acid (sUA), and is an investigational agent now in phase III clinical trial for treatment of gout. In top-line results from a Phase III study on gout patients who did not obtain benefits from treatment with allopurinol and febuxostat, lesinurad alone significantly reduced serum levels of uric acid.

Lesinurad is known by its chemical name as 2-((5-bromo-4-(4-cyclopropylnaphthalen-1-yl)-4H-1,2,4-triazol-3-yl)thio)acetic acid, having the structure of Formula I:

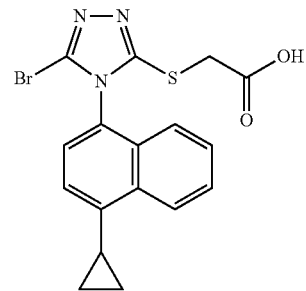

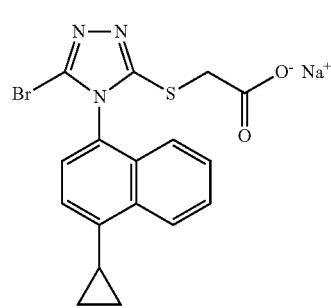

Two crystalline forms of lesinurad have been reported. (WO2012092395) In addition, polymorphic, crystalline and mesophase forms of lesinurad sodium salt (formula II) have also been reported. (WO2011085009) However, due to unpredictable properties of different crystalline forms for a specific compound, new crystalline forms of lesinurad and its sodium salt, in particular their stable polymorphs with superior pharmacological properties, and convenient methods to prepare them remain a great need.

SUMMARY OF THE INVENTION

The present inventors surprisingly discovered new crystalline forms of lesinurad and its sodium salt, which have desired pharmacological properties useful for pharmaceutical development and can be prepared readily in environmentally friendly solvent systems.

In one aspect, the present invention provides crystalline forms of lesinurad, designated as Forms III, IV, V, and VI, respectively.

In another aspect, the present invention provides processes for preparation of Forms III, IV, V, and VI of lesinurad.

In another aspect, the present invention provides crystalline forms of lesinurad sodium salt, designated as Forms α, β, γ, and δ, respectively.

In another aspect, the present invention provides processes for preparation of Forms α, β, γ, and δ of lesinurad sodium salt.

In another aspect, the present invention provides solid pharmaceutical compositions comprising any of crystalline forms III, IV, V, and VI of lesinurad and crystalline forms α, β, γ, and δ of lesinurad sodium salt, or any of combinations thereof.

In another aspect, the present invention provides methods of using any of crystalline forms III, IV, V, and VI of lesinurad and crystalline forms α, β, γ, and δ of lesinurad sodium salt, or any of combinations thereof, in the manufacture of a medicament for treating or delaying the progression or onset of a disease or disorder in connection with activity of a uric acid transporter 1 (URAT1) protein.

In another aspect, the present invention provides methods of treating or delaying the progression or onset of a disease or disorder in connection with activity of a URAT1 protein, comprising administering to a subject in need thereof a pharmaceutical composition comprising any of crystalline forms III, IV, V, and VI of lesinurad and crystalline forms α, β, γ, and δ of lesinurad sodium salt, or any of combinations thereof.

In another aspect, the present invention provides a kit for the treatment of a disease or disorder in connection with activity of a URAT1 protein, comprising a pharmaceutical composition comprising any of crystalline forms III, IV, V, and VI of lesinurad and crystalline forms α, β, γ, and δ of lesinurad sodium salt, or any of combinations thereof, in a container and, optionally, instructions describing use.

Other aspects and embodiments of the present invention will be further illustrated in the following description and examples.

DETAILED DESCRIPTION OF THE INVENTION

The present invention is based on a surprising discovery that lesinurad and its sodium salt can exist in different crystalline forms, and these forms can be prepared readily from environmentally friendly solvent systems using relatively simple processes.

In an aspect, the present invention provides a crystalline form of lesinurad, designated as Form III.

In one embodiment, the crystalline Form III is characterized by an X-ray powder diffraction pattern comprising the following 2θ values measured using CuKα radiation: 20.8°±0.2°, 23.8°±0.2°, and 11.9°±0.2°.

In another embodiment, the crystalline Form III is characterized by an X-ray powder diffraction pattern further comprising the following 2θ values measured using CuKα radiation: 17.8°±0.2°, 24.0°±0.2°, and 27.2°±0.2°.

In another embodiment, the crystalline Form III is characterized by an X-ray powder diffraction pattern further comprising the following 2θ values measured using CuKα radiation: 7.9°±0.2°, 15.3°±0.2°, 17.4°±0.2°, and 22.4°±0.2°.

Figure 1:
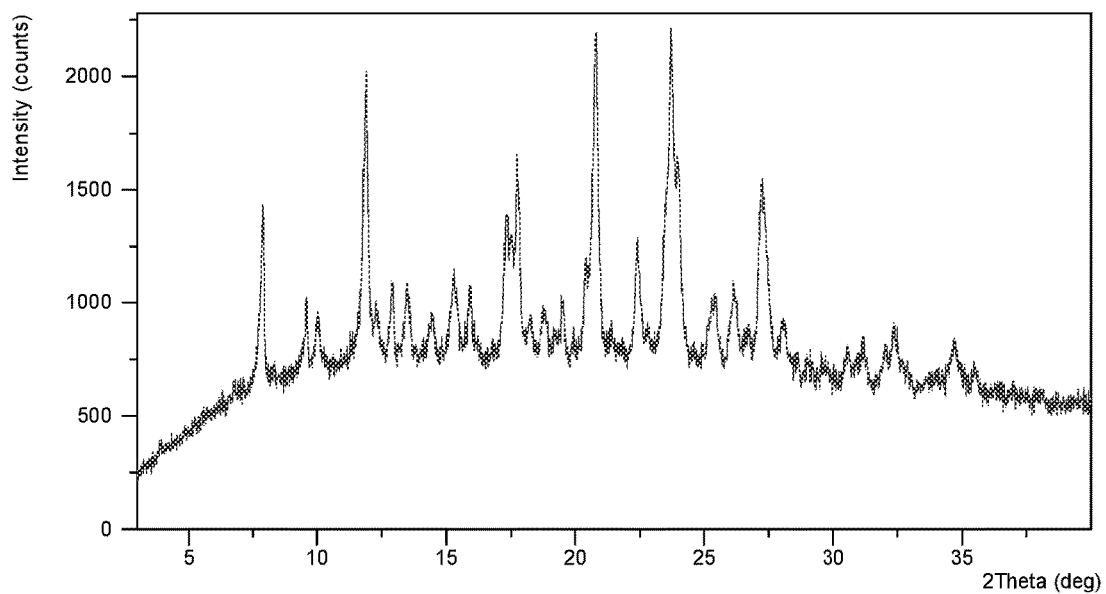
FIG. 1 shows an X-ray powder diffraction (XRPD) pattern of crystalline Form III.

In another embodiment, the crystalline Form III has an X-ray powder diffraction pattern substantially as shown in FIG. 1.

Figure 2:
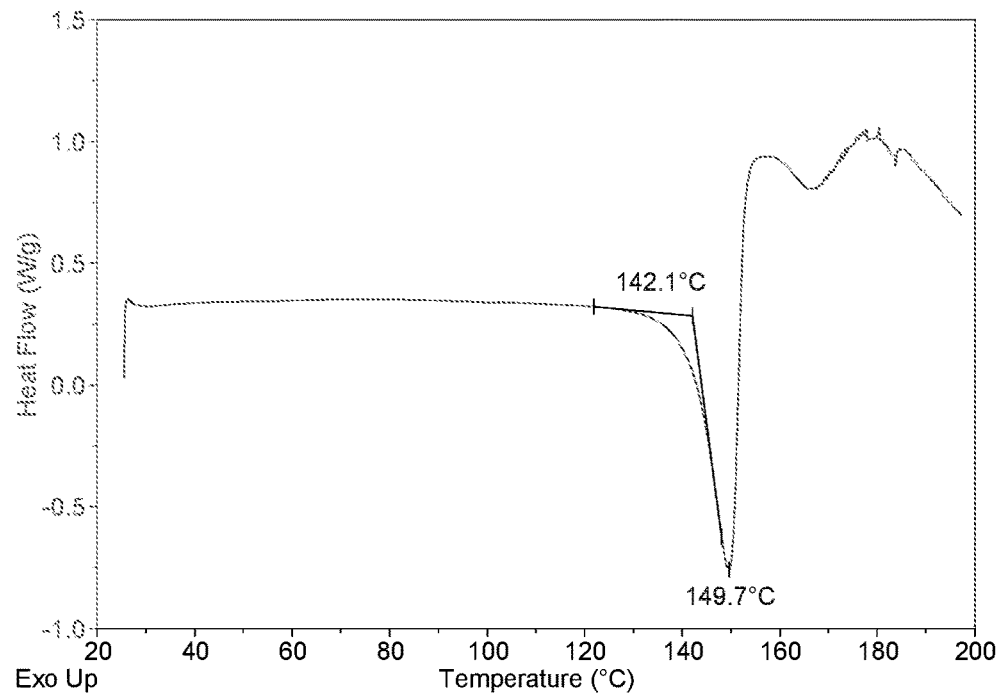
FIG. 2 shows a differential scanning calorimetry (DSC) thermogram of crystalline Form III.

In another embodiment, the crystalline Form III has a differential scanning calorimetry thermogram substantially as shown in FIG. 2, which exhibits an endothermic peak at about 142.1° C.

In another embodiment, the crystalline Form III has a thermal gravimetric analysis thermogram that exhibits about 1.1% weight loss when heated up to 120° C.

Figure 3:
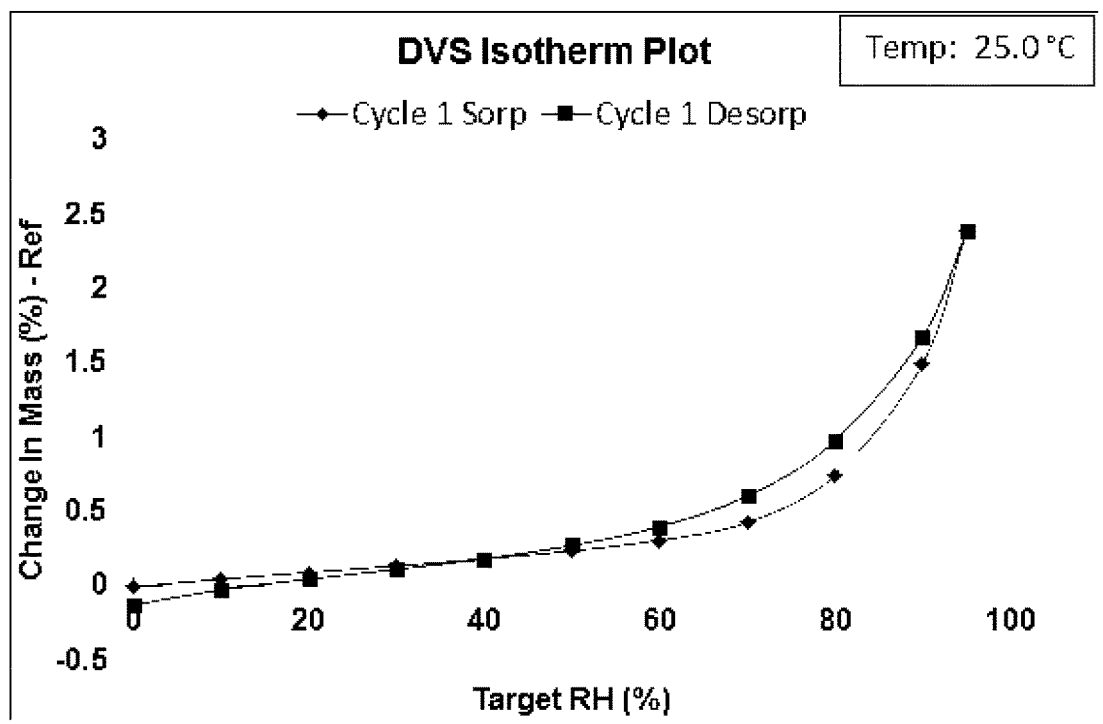
FIG. 3 shows a dynamic vapor sorption (DVS) isotherm plot of crystalline Form III.

In another embodiment, the crystalline Form III has a dynamic vapor sorption (DVS) isotherm plot substantially as shown in FIG. 3.

In some embodiment, Form III is unsolvated. In some embodiment, Form III is anhydrous.

In another aspect, the present invention provides a crystalline form of lesinurad, designated as Form IV.

In one embodiment, the crystalline Form IV is characterized by an X-ray powder diffraction pattern comprising the following 2θ values measured using CuKα radiation: 6.8°±0.2°, 18.5°±0.2°, and 24.6°±0.2°.

In another embodiment, the X-ray powder diffraction pattern of crystalline Form IV further comprises the following 2θ values measured using CuKα radiation: 24.1°±0.2°, 25.0°±0.2°, and 26.7°±0.2°.

In another embodiment, the X-ray powder diffraction pattern of crystalline Form IV further comprises the following 2θ values measured using CuKα radiation: 11.3°±0.2°, 19.0°±0.2°, 21.9°±0.2°, and 20.6°±0.2°.

Figure 4:
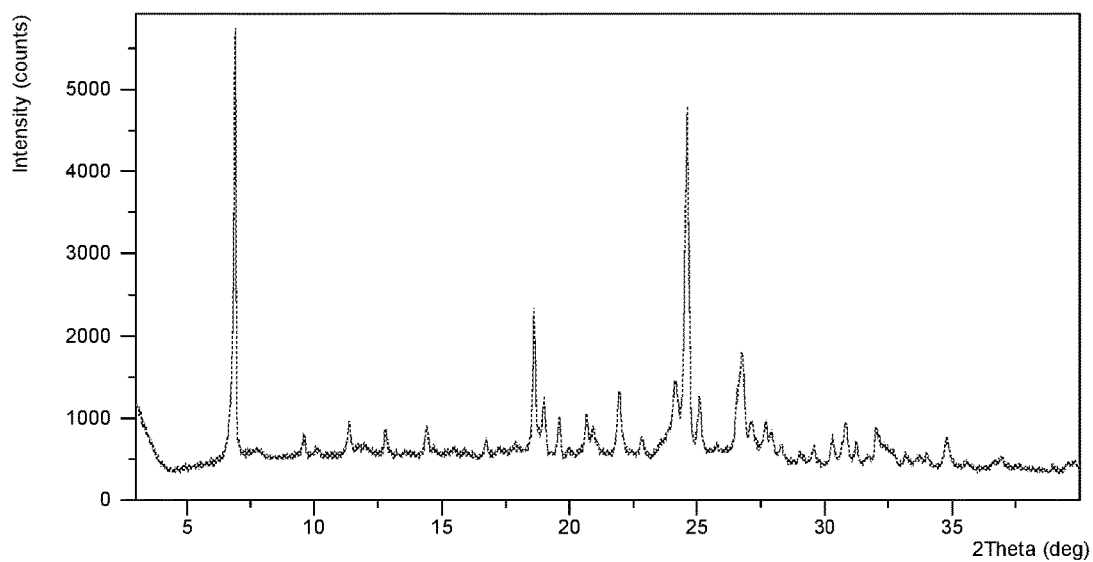
FIG. 4 shows an X-ray powder diffraction (XRPD) pattern of crystalline Form IV.

In another embodiment, the crystalline Form IV has an X-ray powder diffraction pattern substantially as shown in FIG. 4.

Figure 5:
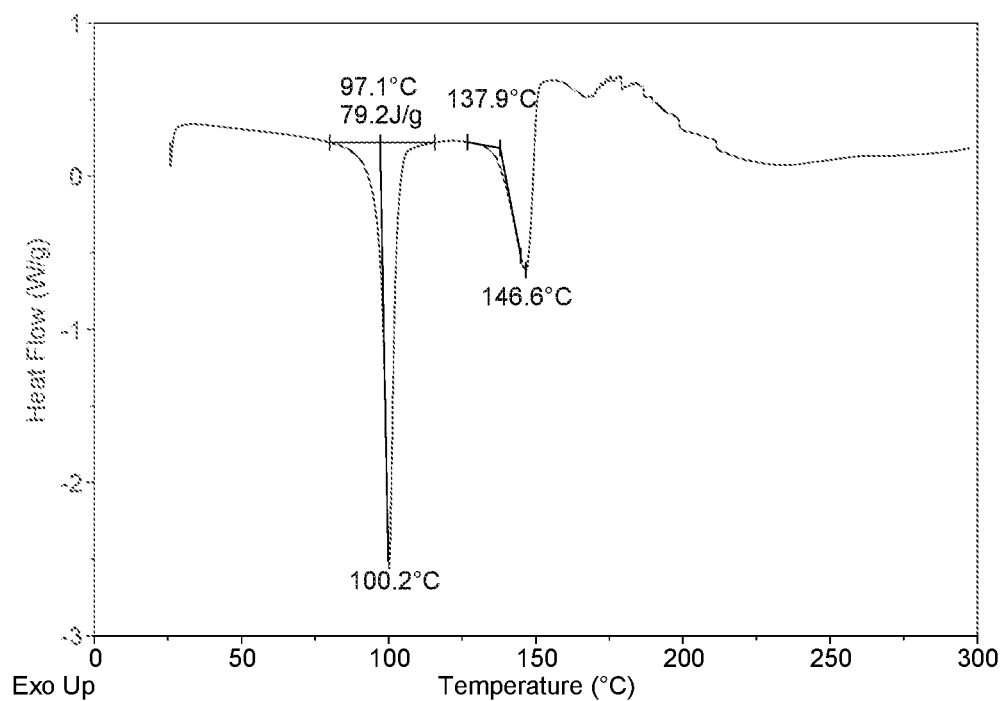
FIG. 5 shows a differential scanning calorimetric (DSC) thermogram of crystalline Form IV.

In another embodiment, the crystalline Form IV has a differential scanning calorimetry thermogram comprising two endothermic peaks at about 97.1° C. and about 137.9° C., respectively, substantially as shown in FIG. 5.

In another embodiment, the crystalline Form IV has a thermal gravimetric analysis (TGA) thermogram comprising about 12.8% weight loss up to 110° C.

In some embodiment, Form IV is solvated. In some embodiment, Form IV is solvated with dichloromethane.

In another aspect, the present invention provides a crystalline form of lesinurad, designated as Form V.

In one embodiment, the crystalline Form V is characterized by an X-ray powder diffraction pattern comprising the following 2θ values measured using CuKα radiation: 20.9°+0.2°, 6.1°+0.2°, and 26.2°+0.2°.

In another embodiment, the X-ray powder diffraction pattern of crystalline Form V further comprises the following 2θ values measured using CuKα radiation: 24.8°±0.2°, 18.7°+0.2°, and 20.1°+0.2°.

In another embodiment, the X-ray powder diffraction pattern of crystalline Form V further comprises the following 2θ values measured using CuKα radiation: 14.6°±0.2°, 17.2°+0.2°, 19.4°+0.2°, and 23.6°+0.2°.

Figure 7:
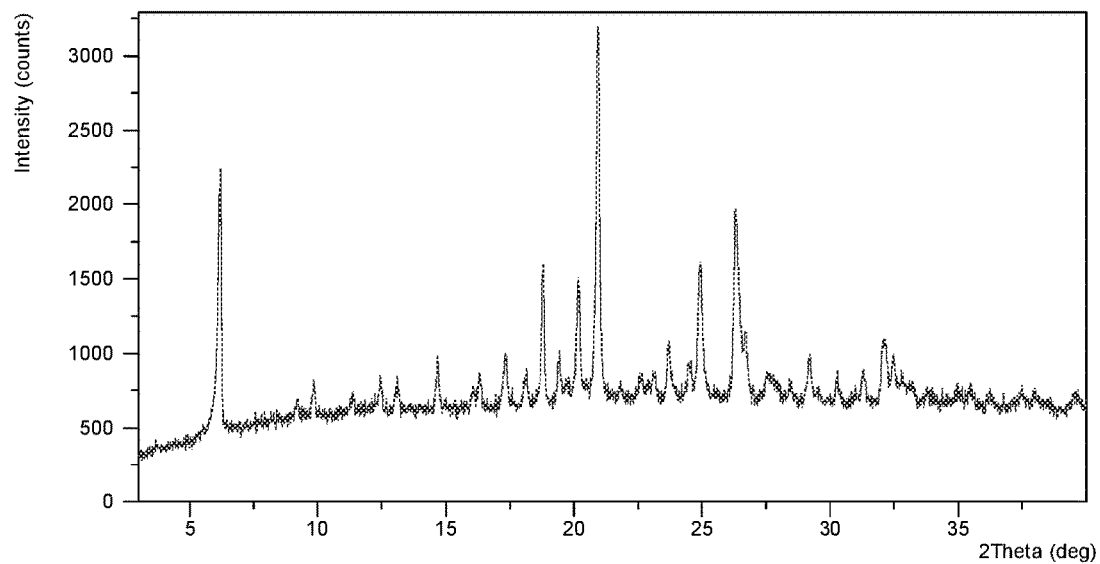
FIG. 7 shows an X-ray powder diffraction (XRPD) pattern of crystalline Form V.

In another embodiment, the crystalline Form V has an X-ray powder diffraction pattern substantially as shown in FIG. 7.

Figure 8:
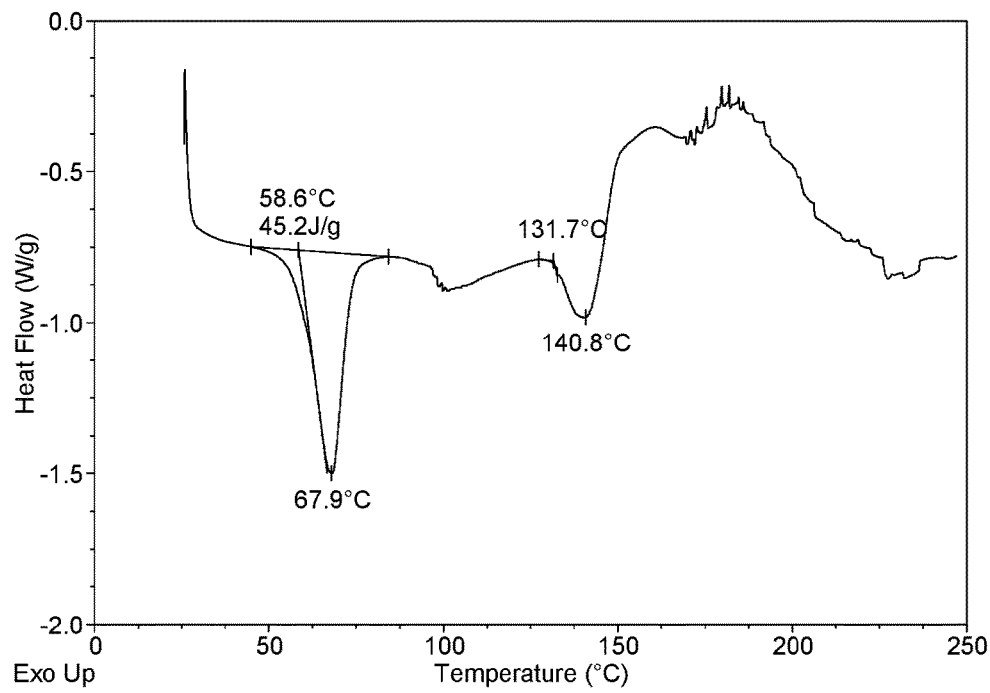
FIG. 8 shows a differential scanning calorimetric (DSC) thermogram of crystalline Form V.

In another embodiment, the crystalline Form V has a differential scanning calorimetry thermogram comprising two endothermic peaks at about 58.6° C. and about 131.7° C., respectively, substantially as shown in FIG. 8.

In another embodiment, the crystalline Form V has a thermal gravimetric analysis (TGA) thermogram comprising about 11.0% weight loss up to 135° C.

In some embodiment, Form V is solvated. In some embodiment, Form V is solvated with 2-methyl tetrahydrofuran.

In another aspect, the present invention provides a crystalline form of lesinurad, designated as Form VI.

In one embodiment, the crystalline Form VI is characterized by an X-ray powder diffraction pattern comprising the following 2θ values measured using CuKα radiation: 23.5°+0.2°, 6.6°+0.2°, and 18.3°+0.2°.

In another embodiment, the X-ray powder diffraction pattern of crystalline Form VI further comprises the following 2θ values measured using CuKα radiation: 17.9°±0.2°, 21.3°+0.2°, and 27.7°+0.2°.

In another embodiment, the X-ray powder diffraction pattern of crystalline Form VI further comprises the following 2θ values measured using CuKα radiation: 11.2°±0.2°, 23.8°+0.2°, 25.1°+0.2°, and 29.6°+0.2°.

Figure 9:
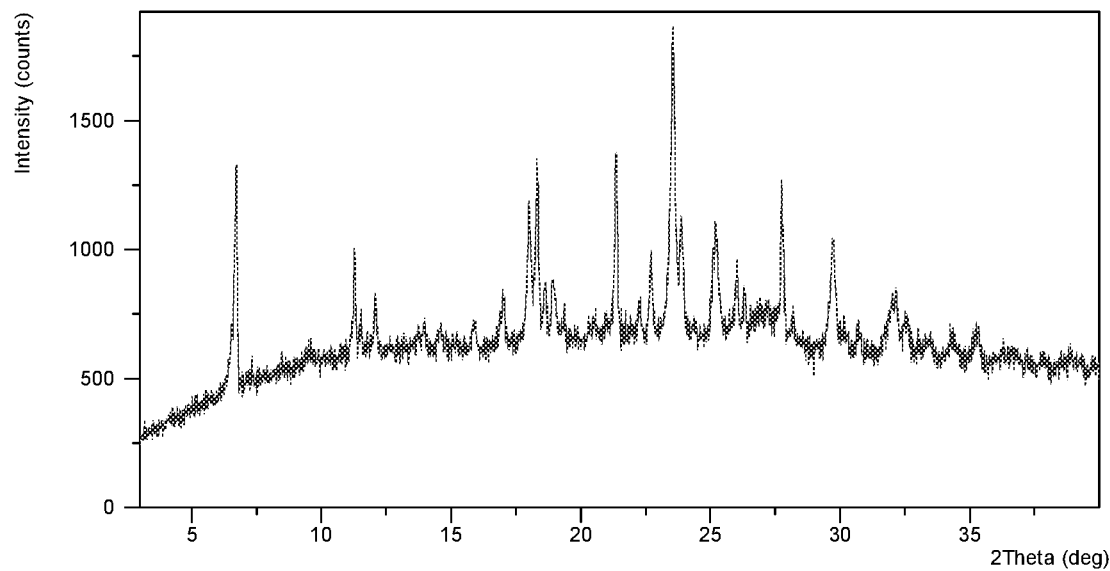
FIG. 9 shows an X-ray powder diffraction (XRPD) pattern of crystalline Form VI.

In another embodiment, the crystalline Form VI has an X-ray powder diffraction pattern substantially as shown in FIG. 9.

Figure 10:
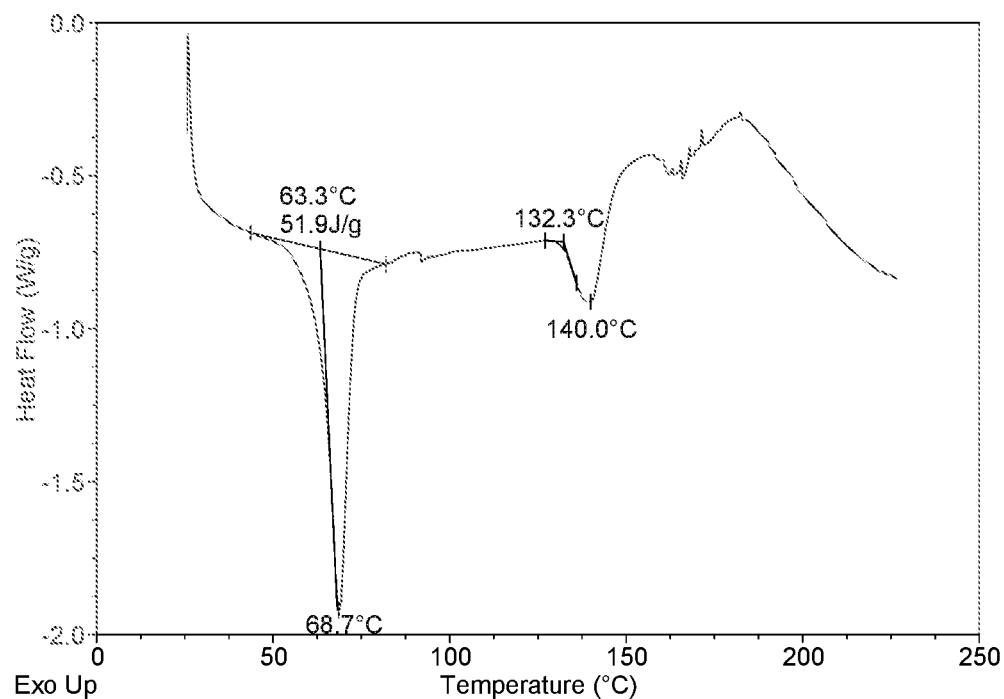
FIG. 10 shows a differential scanning calorimetric (DSC) thermogram of crystalline Form VI.

In another embodiment, the crystalline Form VI has a differential scanning calorimetry thermogram comprising two endothermic peaks at about 63.3° C. and about 132.3° C., respectively, substantially as shown in FIG. 10.

In another embodiment, the crystalline Form VI has a thermal gravimetric analysis (TGA) thermogram comprising about 6.4% weight loss up to 74° C.

In some embodiment, Form VI is solvated. In some embodiment, Form VI is solvated with trichloromethane.

In another aspect, the present invention provides a process for preparation of lesinurad Forms III, IV, V, or VI, which comprises: 1) dissolving lesinurad in one or two solvents selected from the group consisting of alcohols, alkylketones, esters, ethers, aromatic hydrocarbons, nitriles, and water to form a solution; and (2) crystallizing or precipitating lesinurad solid as Form III, IV, V, or VI through stirring, evaporating solvent(s), cooling, adding anti-solvent(s), and/or seeding.

In one embodiment, the solvent is acetonitrile, ethyl acetate, toluene or any of their mixtures, and the crystallization method is slow evaporation of solvent(s) to obtain Form III.

In another embodiment, the solvent is dichloromethane, and the crystallization method is slow evaporation of solvent to obtain Form IV.

In another embodiment, the solvent is 2-methyl tetrahydrofuran, and the crystallization method is slow evaporation of solvent to obtain Form V.

In another embodiment, the solvent is trichloromethane, and the crystallization method is slow evaporation of solvent to obtain Form VI.

In another aspect, the present invention provides a crystalline form of lesinurad sodium salt, designated as Form α.

In one embodiment, the lesinurad sodium salt Form α is characterized by an X-ray powder diffraction pattern comprising the following 2θ values measured using CuKα radiation: 22.8°±0.2°, 25.1°±0.2°, and 17.6°±0.2°.

In another embodiment, the lesinurad sodium salt Form α is characterized by an X-ray powder diffraction pattern further comprising the following 2θ values measured using CuKα radiation: 7.6°±0.2°, 27.9°±0.2°, and 21.2°±0.2°.

In another embodiment, the lesinurad sodium salt Form α is characterized by an X-ray powder diffraction pattern further comprising the following 2θ values measured using CuKα radiation: 25.6°±0.2°, 28.8°±0.2°, 27.1°±0.2°, and 6.8°±0.2°.

Figure 12:
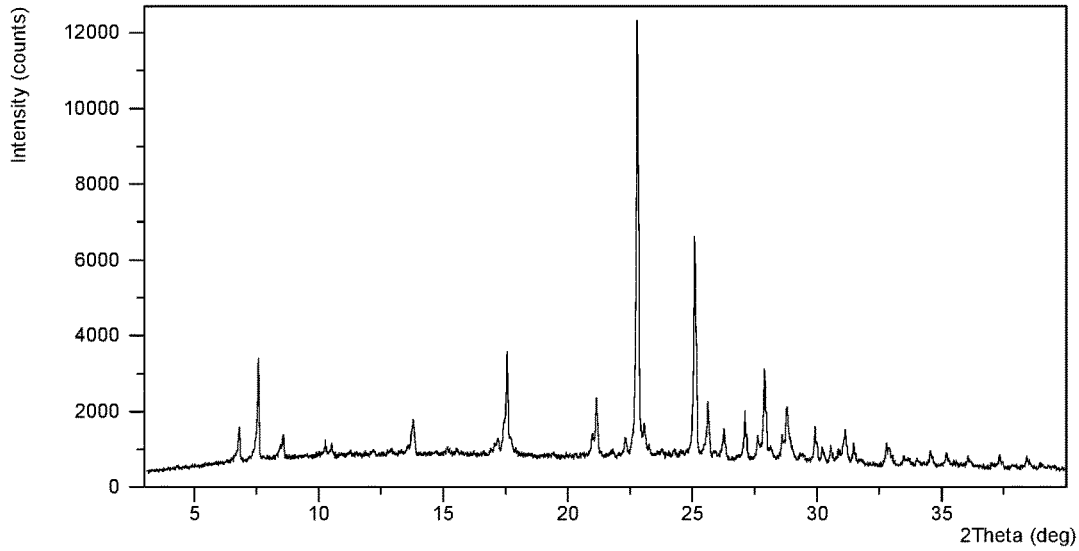
FIG. 12 shows an X-ray powder diffraction (XRPD) pattern of Form α of lesinurad sodium salt.

In another embodiment, the lesinurad sodium salt Form α has an X-ray powder diffraction pattern substantially as shown in FIG. 12.

Figure 13:
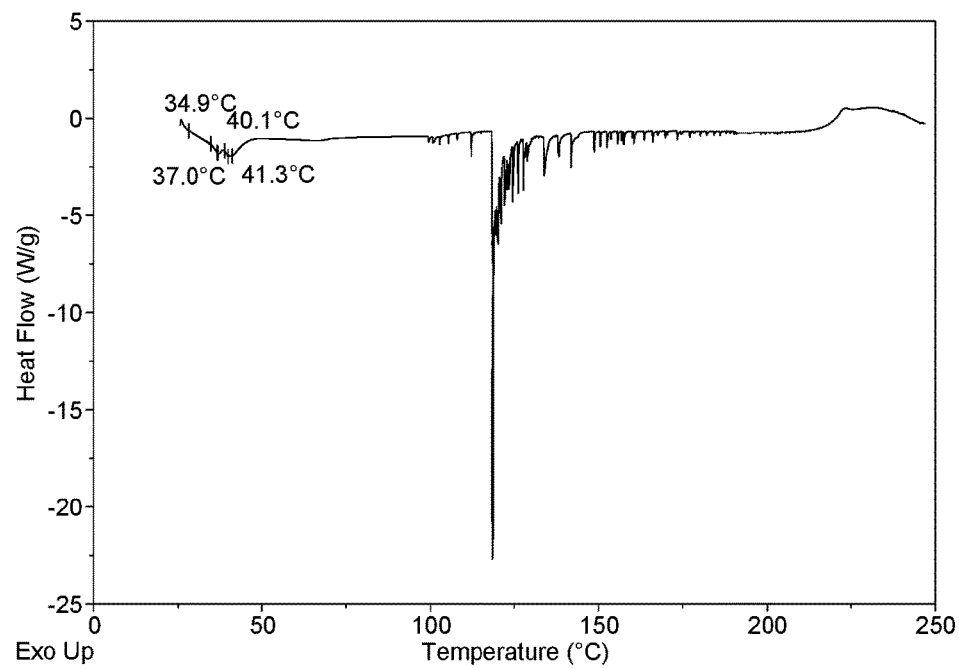
FIG. 13 shows a differential scanning calorimetry (DSC) thermogram of Form α of lesinurad sodium salt.

In another embodiment, the lesinurad sodium salt Form α has a differential scanning calorimetry thermogram substantially as shown in FIG. 13, which exhibits two endothermic peaks at about 34.9° C. and 40.1° C.

In another embodiment, the lesinurad sodium salt Form α has a thermal gravimetric analysis (TGA) thermogram that exhibits about 22.7% weight loss when heated up to 110° C.

In some embodiment, lesinurad sodium salt Form α is solvated. In some embodiment, lesinurad sodium salt Form α is a hydrate.

In another aspect, the present invention provides a crystalline form of lesinurad sodium salt, designated as Form β.

In one embodiment, the lesinurad sodium salt Form β is characterized by an X-ray powder diffraction pattern comprising the following 2θ values measured using CuKα radiation: 9.2°±0.2°, 23.1°±0.2°, and 18.5°±0.2°.

In another embodiment, the X-ray powder diffraction pattern of lesinurad sodium salt Form β further comprises the following 2θ values measured using CuKα radiation: 4.6°±0.2°, 23.6°±0.2°, and 12.9°±0.2°.

In another embodiment, the X-ray powder diffraction pattern of lesinurad sodium salt Form β further comprises the following 2θ values measured using CuKα radiation: 29.9°±0.2°, 25.2°±0.2°, 21.8°±0.2°, and 28.5°±0.2°.

Figure 15:
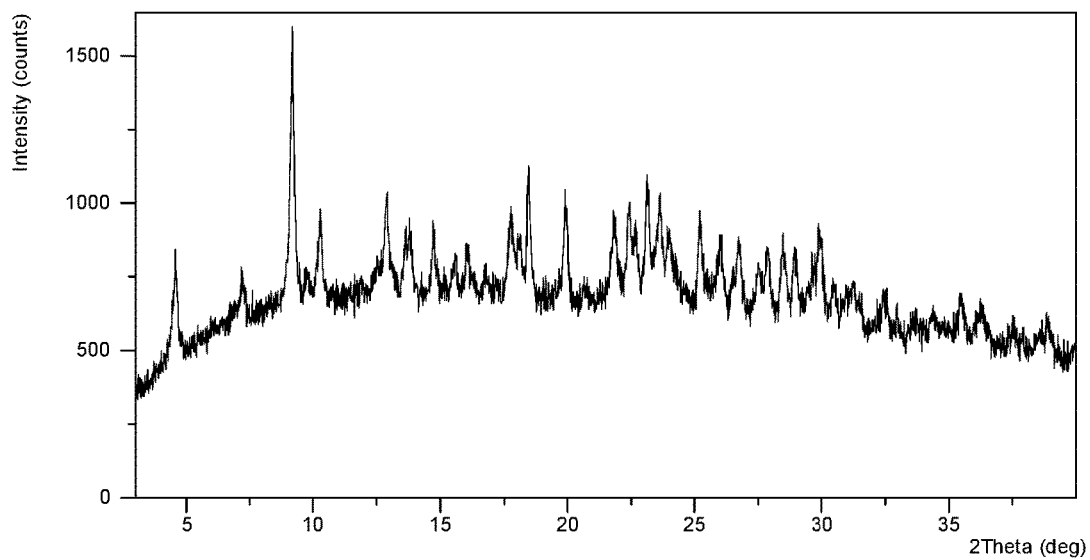
FIG. 15 shows an X-ray powder diffraction (XRPD) pattern of Form β of lesinurad sodium salt.

In another embodiment, the lesinurad sodium salt Form β has an X-ray powder diffraction pattern substantially as shown in FIG. 15.

Figure 16:
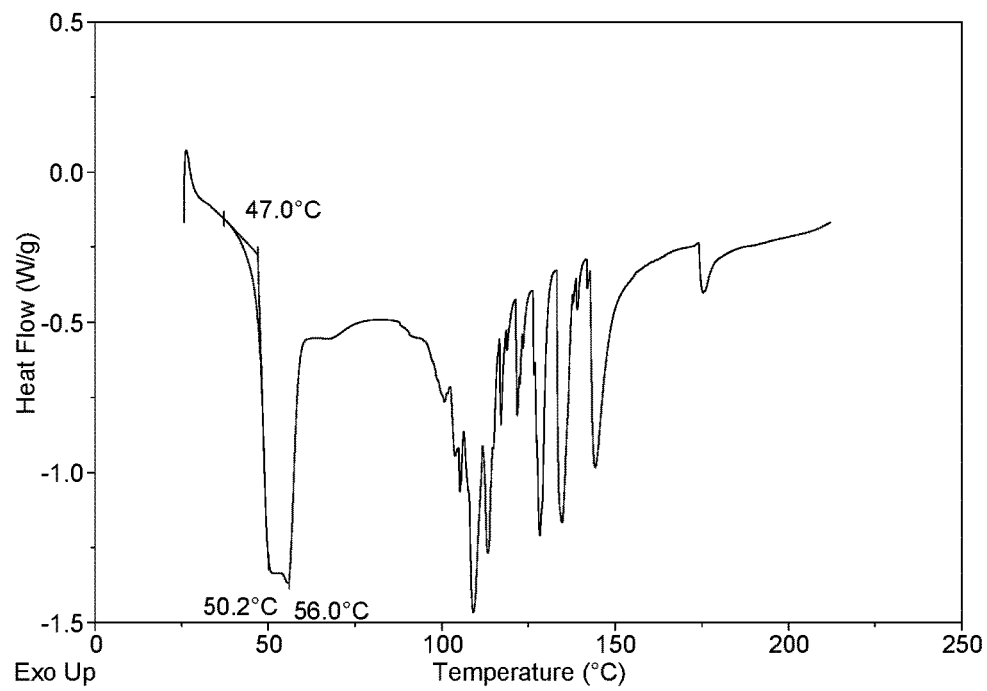
FIG. 16 shows a differential scanning calorimetric (DSC) thermogram of Form β of lesinurad sodium salt.

In another embodiment, the lesinurad sodium salt Form β has a differential scanning calorimetry thermogram comprising two endothermic peaks at about 47.0° C. and about 56.0° C., respectively, substantially as shown in FIG. 16.

In another embodiment, the lesinurad sodium salt Form β has a thermal gravimetric analysis (TGA) thermogram comprising about 14.6% weight loss up to 100° C.

In some embodiment, lesinurad sodium salt Form β is solvated. In some embodiment, lesinurad sodium salt Form β is a hydrate.

In another aspect, the present invention provides a crystalline form of lesinurad sodium salt, designated as Form γ.

In one embodiment, the lesinurad sodium salt Form γ is characterized by an X-ray powder diffraction pattern comprising the following 2θ values measured using CuKα radiation: 10.4°±0.2°, 4.7°±0.2°, and 9.3°±0.2°.

In another embodiment, the X-ray powder diffraction pattern of lesinurad sodium salt Form γ further comprises the following 2θ values measured using CuKα radiation: 13.0°±0.2°, 23.7°±0.2°, and 25.3°±0.2°.

In another embodiment, the X-ray powder diffraction pattern of lesinurad sodium salt Form γ further comprises the following 2θ values measured using CuKα radiation: 7.3°±0.2°, 17.8°±0.2°, 21.9°±0.2°, and 22.5°±0.2°.

Figure 17:
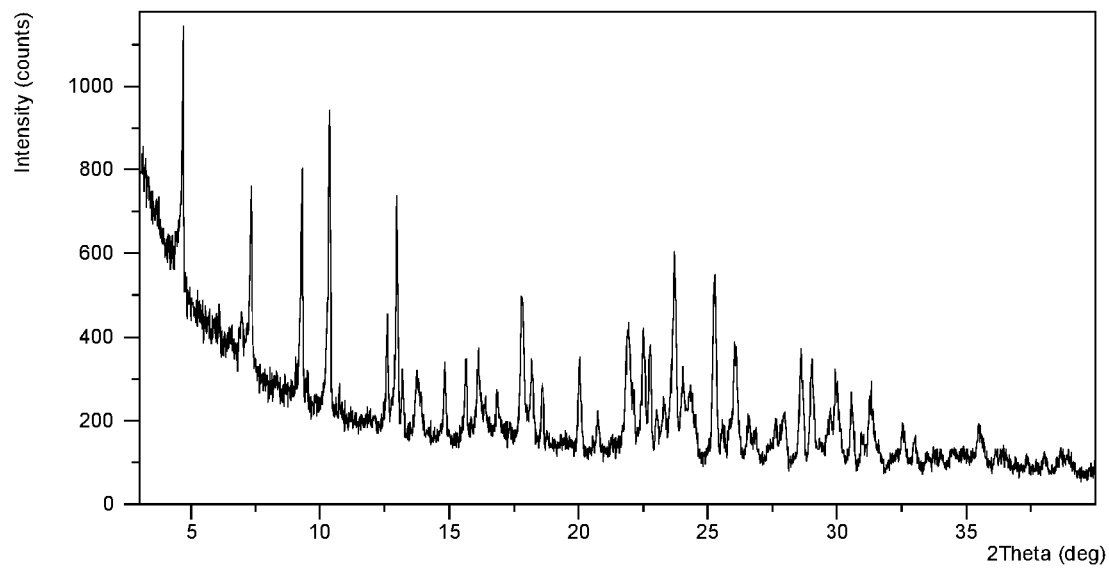
FIG. 17 shows an X-ray powder diffraction (XRPD) pattern of Form γ of lesinurad sodium salt.

In another embodiment, the lesinurad sodium salt Form γ has an X-ray powder diffraction pattern substantially as shown in FIG. 17.

Figure 18:
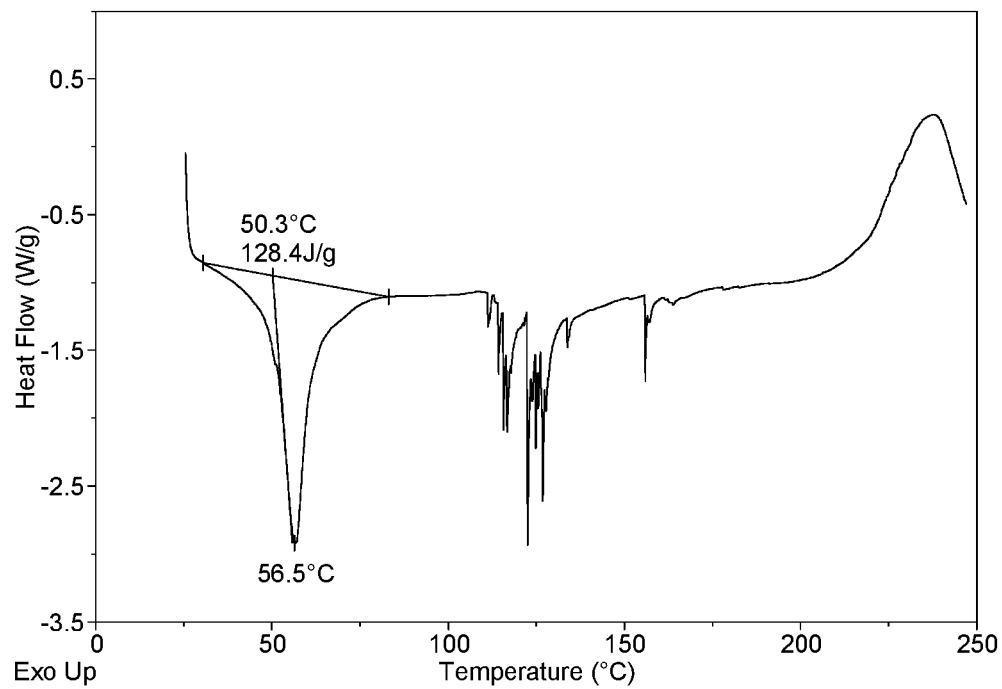
FIG. 18 shows a differential scanning calorimetric (DSC) thermogram of Form γ of lesinurad sodium salt.

In another embodiment, the lesinurad sodium salt Form γ has a differential scanning calorimetry thermogram comprising an endothermic peak at about 50.3° C. substantially as shown in FIG. 18.

In another embodiment, the lesinurad sodium salt Form γ has a thermal gravimetric analysis (TGA) thermogram comprising about 16.5% weight loss up to 78° C.

In another aspect, the present invention provides a crystalline form of lesinurad sodium salt, designated as Form δ.

In one embodiment, the lesinurad sodium salt Form δ is characterized by an X-ray powder diffraction pattern comprising the following 2θ values measured using CuKα radiation: 9.0°±0.2°, 18.2°±0.2°, and 22.9°±0.2°.

In another embodiment, the X-ray powder diffraction pattern of lesinurad sodium salt Form δ further comprises the following 2θ values measured using CuKα radiation: 4.5°±0.2°, 13.7°±0.2°, 27.5°±0.2°, and 29.4°±0.2°.

Figure 19:
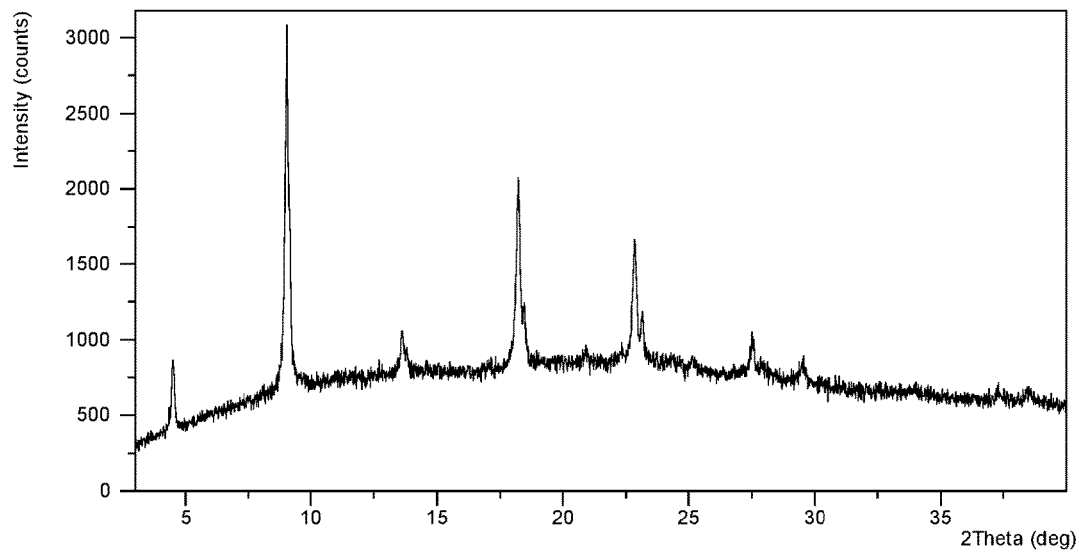
FIG. 19 shows an X-ray powder diffraction (XRPD) pattern of Form δ of lesinurad sodium salt.

In another embodiment, the lesinurad sodium salt Form δ has an X-ray powder diffraction pattern substantially as depicted in FIG. 19.

In another aspect, the present invention provides a process for preparation of lesinurad sodium salt Forms α, β, γ, or δ, which comprises (1) dissolving lesinurad sodium salt in one or two solvents selected from the group consisting of alcohols, alkylketones, esters, ethers, and water to form a solution; and (2) crystallizing or precipitating lesinurad sodium salt solid as Form α, β, γ, or δ through slurrying/stirring, evaporating said solvent(s), cooling the solution, adding anti-solvent(s), and/or seeding.

In one embodiment, the solvent is water, and the crystallization method is slurrying/stirring to obtain Form α of lesinurad sodium salt.

In another embodiment, the solvent is a mixture of ethyl acetate and water, and the crystallization method is slurrying/stirring to obtain Form β.

In another embodiment, the solvent is ethyl acetate or toluene, and the crystallization method is slow evaporation of the solvent(s) to obtain Form γ.

In another embodiment, the solvent is a mixture of 2-methyl tetrahydrofuran and water, the crystallization method is heating the solution to an elevated temperature (e.g., above 50° C., for example, 60° C.-80° C.), then cooling the solution to precipitate out lesinurad sodium salt as Form δ.

In another aspect, the present invention provides solid pharmaceutical compositions, comprising any one or combination of the crystalline forms of lesinurad and crystalline forms of lesinurad sodium salt described herein.

Crystalline forms of lesinurad or lesinurad sodium salt, together with one or more pharmaceutically acceptable excipients, of the present invention may be further formulated as: solid oral dosage forms such as, but not limited to, powders, granules, pellets, tablets, and capsules; liquid oral dosage forms such as, but not limited to, syrups, suspensions, dispersions, and emulsions; and injectable preparations such as, but not limited to, solutions, dispersions, and freeze dried compositions. Formulations may be in the forms of immediate release, delayed release or modified release. Further, immediate release compositions may be conventional, dispersible, chewable, mouth dissolving, or flash melt preparations; and modified release compositions may comprise hydrophilic or hydrophobic, or combinations of hydrophilic and hydrophobic, release rate controlling substances to form matrix or reservoir, or combination of matrix and reservoir systems. The compositions may be prepared using techniques such as direct blending, dry granulation, wet granulation, and extrusion and spheronization. Compositions may be presented as uncoated, film coated, sugarcoated, powder coated, enteric coated, or modified release coated.

In another aspect, the present invention provides methods of using crystalline forms of lesinurad or crystalline forms of lesinurad sodium, or any combination thereof, in the manufacture of a medicament for treating or delaying the progression or onset of a disease or disorder in connection with activity of a URAT1 protein.

In another aspect, the present invention provides methods of treating or delaying the progression or onset of a disease or disorder in connection with activity of a URAT1 protein, comprising administering to a subject in need thereof a pharmaceutical composition comprising any of the crystalline forms of lesinurad and/or crystalline forms of lesinurad sodium salt as described herein.

In another aspect the present invention provides kits for the treatment of diseases and disorders, such as the ones described herein. These kits comprise any of the crystalline forms of lesinurad or its sodium salt, or combination or pharmaceutical composition thereof, in a container and, optionally, instructions describing the use of the kit according to the various methods described herein. Such kits may also include information, such as scientific literature references, package insert materials, clinical trial results, or the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kits described herein may be used directly by a patient or consumer according to the instructions included therein or according to directions provided by a physician, nurse, or pharmacist, or the like.

The diseases and disorders in connection with the activity of a URAT1 protein, as referred to anywhere in this application, include, but are not limited to, polycythemia, myeloid metaplasia, gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis, and sarcoidosis.

In a preferred embodiment, the disease or disorder is hyperuricaemia, gout, or gouty arthritis.

The term "subject", as used herein, refers to a mammalian or non-mammalian animal. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment of the methods and compositions provided herein, the mammalian animal is a human. In another embodiment, the mammalian animal is a domestic animal, such as a dog, cat, or horse.

The terms "effective amount," "therapeutically effective amount" and the like, as used herein, refer to an amount of any of the crystalline forms of lesinurad or its sodium salt being administered that is sufficient to cause biologically or clinically significant effect on a subject in the treatment or prevention of a particular disease or condition. The result can be reduction and/or alleviation of the signs, symptoms, or causes of a disease, or any other desired alteration of a biological system. For example, an "effective amount" for therapeutic uses is the amount of the composition comprising a crystal form as disclosed herein required to provide a clinically significant decrease in a disease. An appropriate "effective" amount in any individual case may be determined using techniques known to a person skilled in the art. The term "substantially," when referring to a characteristic figure of a crystal form, such as an XRPD pattern, a DSC thermogram, or the like, means that a subject figure may be non-identical to the reference depicted herein, but it falls within the limits of experimental error and thus may be deemed as derived from the same crystal form as disclosed herein, as judged by a person of ordinary skill in the art.

The following non-limiting examples will further illustrate certain aspects of the present invention.

EXAMPLES

X-Ray Powder Diffraction (XRPD)

Analytical Instrument: Panalytical Empyrean. The X-ray powder diffractogram was determined by mounting a sample of the crystalline material on a Si single crystal low-background holder and spreading out the sample into a thin layer with the aid of a microscope slide. The 2θ position was calibrated against Panalytical 640 Si powder standard. The sample irradiated with X-rays generated by a copper long-fine focus tube operated at 45 kV and 40 mA with a wavelength of Kα1=1.540589 angstroms and Kα2=1.544426 angstroms (Kα1/Kα2 intensity ratio is 0.50). The collimated X-ray source was passed through a programmed divergence slit set at 10 mm and the reflected radiation directed through a 5.5 mm anti-scattering slit. The sample was exposed for 16.3 seconds per 0.013° 2-theta increment (continuous scan mode) over the range 3 degrees to 40 degrees 2-theta in theta-theta mode. The running time was 3 minutes and 57 seconds. The instrument was equipped with an RTMS detector (X'Celerator). Control and data capture was accomplished by means of a Dell Optiplex 780 XP operating with data collector software.

Persons skilled in the art of X-ray powder diffraction will realize that the relative intensity of peaks can be affected by, for example, grains above 30 microns in size and non-unitary aspect ratios that may affect analysis of samples. The skilled person will also realize that the position of reflections can be affected by the precise height at which the sample sits in the diffractometer and the zero calibration of the diffractometer. The surface planarity of the sample may also have a small effect. Hence, the diffraction pattern data presented are not to be taken as absolute values.

An XRPD pattern of a crystalline form is often described as comprising certain "representative" or "characteristic" peaks or 2θ values, they refer to more prominent peaks, or a subset thereof, in the XRPD pattern. Typically, "characteristic peaks" are defined as a subset of representative (prominent) peaks used to differentiate one crystalline polymorph or form from another crystalline polymorph or form. Characteristic peaks may be determined by evaluating which representative peaks, if any, are present in one crystalline polymorph of a compound but not in all other known crystalline polymorphs of that compound. However, not all crystalline polymorphs of a compound would necessarily have at least one characteristic peak. As a person of ordinary skill in the art would understand, in certain situations, the overall diffraction pattern should be used to determine whether a crystal form exists as described or claimed.

Differential Scanning Calorimetry (DSC)
  Analytical Instrument: TA Instruments Q2000 DSC.
  Heating rate: 10° C. per minute.
  Purge gas: nitrogen
Thermal Gravimetric Analysis (TGA)
  Analytical Instrument: TA Instruments Q500 TGA.
  Heating rate: 10° C. per minute.
  Purge gas: nitrogen.
Dynamic Vapor Sorption (DVS)
Dynamic Vapor Sorption (DVS) was measured via a SMS (Surface Measurement Systems) DVS Intrinsic. The relative humidity at 25° C. were calibrated against deliquescence point of LiCl, $Mg(NO_3)_2$ and KCl. Typical Parameters for DVS test are listed below.

| Parameters for DVS test | |
|---|---|
| Parameters | Settings/Values |
| Temperature | 25° C. |
| Sample size | 10~20 mg |
| Gas and flow rate | $N_2$, 200 mL/min |
| dm/dt | 0.002%/min |
| Min. dm/dt stability duration | 10 min |
| Max. equilibrium time | 180 min |
| RH range | 0% RH to 95% RH |
| RH step size | 10% RH from 0% RH to 90% RH |
| | 5% RH from 90% RH to 95% RH |

Example 1. Preparation of Lesinurad Crystalline Form III

To 1.0 mL of acetonitrile was added 10 mg of lesinurad. The mixture was filtered, and the clear filtrate was evaporated slowly under ambient conditions until precipitation. The solid was isolated and Form III was obtained, which was analyzed by XRPD, DSC, and TGA. The XRPD data of the Form III obtained in this example are listed in Table 1.

The XRPD pattern, DSC thermogram, and DVS isotherm plot of Form III obtained from this example are displayed in FIGS. 1, 2, and 3, respectively. The thermal gravimetric analysis of the sample showed weight loss of only about 1% when heated to 120° C., indicating that the sample is not a solvate, but likely anhydrous.

TABLE 1

| 2 theta | d spacing | intensity % |
|---------|-----------|-------------|
| 7.95 | 11.13 | 51.65 |
| 9.52 | 9.29 | 17.28 |
| 10.04 | 8.81 | 21.60 |
| 11.93 | 7.42 | 88.11 |
| 12.94 | 6.84 | 30.77 |
| 13.53 | 6.54 | 26.97 |
| 14.46 | 6.12 | 20.53 |
| 15.34 | 5.78 | 30.66 |
| 15.94 | 5.56 | 28.36 |
| 17.36 | 5.11 | 49.37 |
| 17.77 | 4.99 | 63.07 |
| 18.82 | 4.71 | 20.60 |
| 19.55 | 4.54 | 22.36 |
| 20.85 | 4.26 | 100.00 |
| 22.44 | 3.96 | 38.09 |
| 23.76 | 3.75 | 96.80 |
| 24.04 | 3.70 | 59.21 |
| 25.43 | 3.50 | 22.64 |
| 26.21 | 3.40 | 23.03 |
| 27.24 | 3.27 | 52.22 |
| 28.10 | 3.18 | 14.50 |
| 32.42 | 2.76 | 13.55 |
| 34.72 | 2.58 | 12.22 |

Example 2. Preparation of Lesinurad Crystalline Form IV

To 2.0 mL of dichloromethane was added 10 mg of lesinurad. The mixture was filtered, and the clear filtrate was evaporated slowly under ambient conditions until precipitation. The solid was isolated and Form IV was obtained, which was analyzed by XRPD, DSC, and TGA. The XRPD data of the Form IV obtained in this example are listed in Table 2.

The XRPD pattern and DSC thermogram of Form IV obtained from this example are displayed in FIGS. 4 and 5, respectively. The thermal gravimetric analysis (TGA) of the sample showed weight loss of about 12.8% when heated to 110° C., indicating that the sample is likely a dichloromethane solvate.

Figure 6:
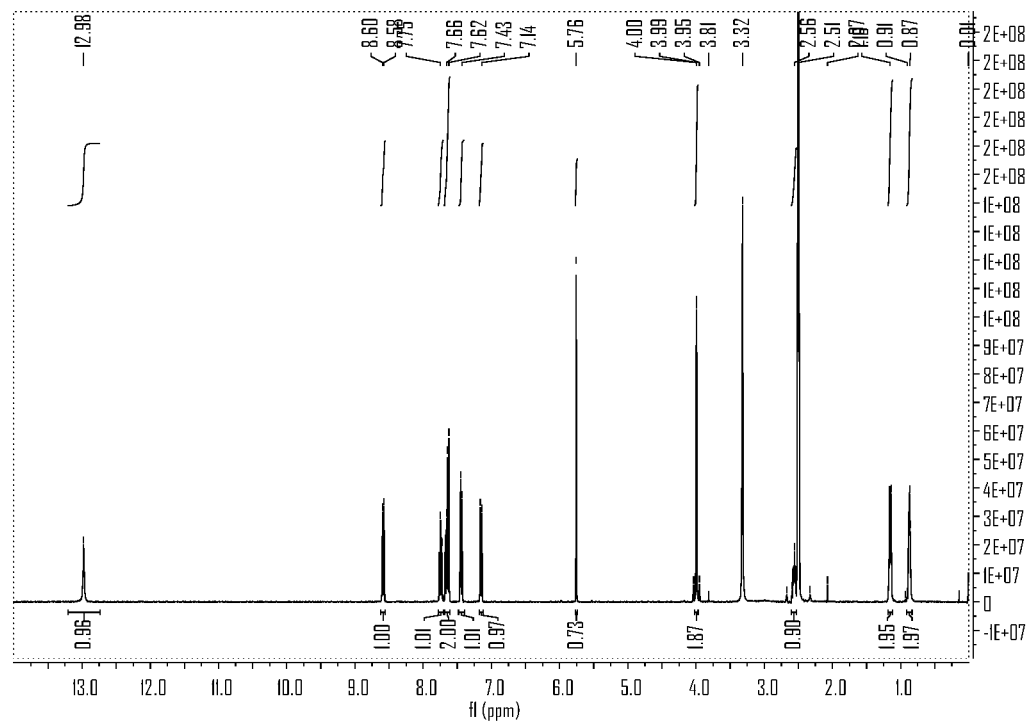
FIG. 6 shows a $^1$H-NMR spectrum of crystalline form IV of lesinurad dissolved in DMSO-$d_6$.

$^1$H-NMR spectrum of the sample, as shown in FIG. 6, also indicates presence of dichloromethane (singlet at δ 5.76 ppm), perhaps in a solvate form of lesinurad, which is consistent with the TGA data. $^1$H NMR (400 MHz, DMSO-$d_6$) of lesinurad: δ 12.98 (s, 1H), 8.59 (d, J=8.4 Hz, 1H), 7.74 (dd, J=11.3, 4.1 Hz, 1H), 7.69-7.61 (m, 2H), 7.44 (d, J=7.6 Hz, 1H), 7.15 (d, J=8.2 Hz, 1H), 3.99 (d, J=1.7 Hz, 2H), 2.56 (td, J=8.5, 4.4 Hz, 1H), 1.19-1.12 (m, 2H), 0.91-0.83 (m, 2H).

TABLE 2

| 2 theta | d spacing | intensity % |
|---------|-----------|-------------|
| 6.83 | 12.95 | 100.00 |
| 9.55 | 9.26 | 6.58 |
| 11.31 | 7.82 | 10.48 |
| 12.74 | 6.95 | 8.46 |
| 14.33 | 6.18 | 9.17 |
| 16.66 | 5.32 | 6.39 |
| 18.54 | 4.79 | 36.44 |
| 18.96 | 4.68 | 16.53 |
| 19.55 | 4.54 | 11.80 |
| 20.62 | 4.31 | 12.35 |
| 21.92 | 4.06 | 17.48 |
| 22.77 | 3.91 | 7.20 |
| 24.10 | 3.69 | 20.48 |
| 24.56 | 3.62 | 83.56 |
| 25.05 | 3.56 | 16.72 |
| 26.73 | 3.34 | 26.44 |
| 27.09 | 3.29 | 11.06 |
| 27.63 | 3.23 | 11.15 |
| 29.50 | 3.03 | 4.91 |
| 30.27 | 2.95 | 7.31 |
| 30.79 | 2.90 | 10.53 |
| 31.20 | 2.87 | 6.36 |
| 31.97 | 2.80 | 9.64 |
| 33.89 | 2.64 | 2.87 |
| 34.73 | 2.58 | 7.22 |
| 36.80 | 2.44 | 2.16 |

Example 3. Preparation of Lesinurad Form V

To 0.3 mL of 2-methyl tetrahydrofuran was added 10 mg of lesinurad. The mixture was filtered, and the clear filtrate was evaporated slowly under ambient conditions until precipitation. The solid was isolated and Form V was obtained, which was analyzed by XRPD, DSC, and TGA. The XRPD data of the Form V obtained in this example are listed in Table 3.

The XRPD pattern and DSC thermogram of Form V obtained from this example are displayed in FIGS. 7 and 8, respectively. The thermal gravimetric analysis of the sample showed weight loss of about 2.55% when heated to 79.0° C., and a total weight loss of about 11.0% when heated to 135.0° C., indicating that the sample was likely a 2-methyl-THF solvate.

TABLE 3

| 2 theta | d spacing | intensity % |
|---------|-----------|-------------|
| 6.12 | 14.44 | 66.05 |
| 9.78 | 9.04 | 8.81 |
| 12.36 | 7.16 | 9.24 |
| 14.59 | 6.07 | 14.26 |
| 16.14 | 5.49 | 6.41 |
| 17.24 | 5.14 | 15.50 |
| 18.03 | 4.92 | 9.37 |
| 18.70 | 4.74 | 36.72 |
| 19.35 | 4.59 | 13.77 |
| 20.10 | 4.42 | 35.37 |
| 20.88 | 4.25 | 100.00 |
| 23.61 | 3.77 | 15.75 |
| 24.42 | 3.65 | 11.35 |
| 24.84 | 3.58 | 38.14 |
| 26.21 | 3.40 | 51.45 |
| 27.56 | 3.24 | 6.61 |
| 29.10 | 3.07 | 11.35 |
| 30.25 | 2.96 | 4.02 |
| 31.22 | 2.86 | 6.80 |
| 31.98 | 2.80 | 15.32 |
| 35.13 | 2.55 | 1.55 |

Example 4. Preparation of Lesinurad Form VI

To 0.4 mL of trichloromethane was added 10 mg of lesinurad. The mixture was filtered, and the clear filtrate was evaporated slowly under ambient conditions until precipitation. The solid was isolated and Form VI was obtained, which was analyzed by XRPD, DSC, and TGA. The XRPD data of the Form VI obtained in this example are listed in Table 4.

The XRPD pattern and DSC thermogram of Form VI obtained from this example are displayed in FIGS. 9 and 10, respectively. The thermal gravimetric analysis of the sample showed weight loss of about 6.4% when heated to 74.0° C., indicating that the sample was likely a trichloromethane solvate.

TABLE 4

| 2 theta | d spacing | intensity % |
|---|---|---|
| 6.64 | 13.31 | 71.42 |
| 11.20 | 7.90 | 31.14 |
| 12.00 | 7.37 | 17.42 |
| 16.92 | 5.24 | 14.20 |
| 17.94 | 4.95 | 45.23 |
| 18.27 | 4.86 | 52.72 |
| 18.87 | 4.70 | 19.71 |
| 21.28 | 4.18 | 57.82 |
| 22.63 | 3.93 | 28.03 |
| 23.47 | 3.79 | 100.00 |
| 23.80 | 3.74 | 41.77 |
| 25.13 | 3.54 | 39.28 |
| 25.93 | 3.44 | 23.55 |
| 27.68 | 3.22 | 47.29 |
| 29.65 | 3.01 | 35.63 |
| 32.06 | 2.79 | 15.97 |
| 35.19 | 2.55 | 7.53 |

Example 5. Stability Assessment of Form III Under Stress Conditions

Figure 11:
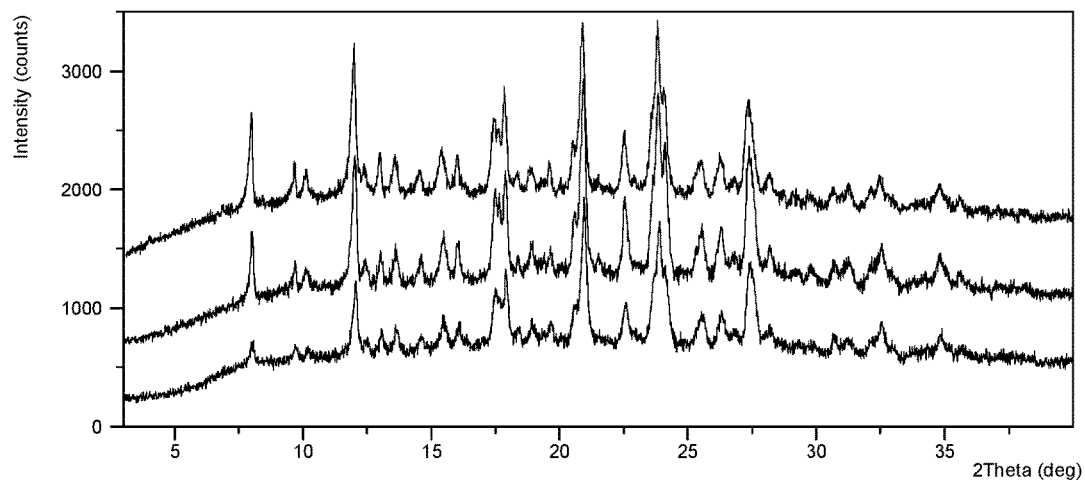
FIG. 11 shows comparison of the XRPD pattern of Form III before storage (top pattern), after being stored under 25° C./60% RH for 14 days (middle pattern), and after being stored under 40° C./75% RH for 14 days (bottom pattern).

Two samples of lesinurad Form III were stored under 25° C./60% RH and 40° C./75% RH, respectively, with dish open for 14 days. The solid samples were analyzed by XRPD. The XRPD patterns of the Form III sample before storage (top pattern), after being stored under 25° C./60% RH for 14 days (middle pattern), and after being stored under 40° C./75% RH for 14 days (bottom pattern) are displayed in FIG. 11. The results of stability assessment tabulated in Table 5 suggest that Form III is stable under the stress conditions.

TABLE 5

| Initial form | Conditions | Storage time | Final form |
|---|---|---|---|
| Form III (top pattern in FIG. 5) | 25° C./60% RH | 14 days | Form III (middle pattern in FIG. 5) |
| Form III (top pattern in FIG. 5) | 40° C./75% RH | 14 days | Form III (bottom pattern in FIG. 5) |

Example 6. Hygroscopicity Assessment of Form III

Hygroscopicity of lesinurad Form III was investigated using dynamic vapor sorption (DVS). The DVS isotherm plot of Form III displayed in FIG. 4 and the detailed data listed in Table 6 show that the sample has 0.8% water uptake under 80% RH, 25° C., suggesting that Form III is slightly hygroscopic.

TABLE 6

| Solid Form | Water uptake under 80% RH | Water uptake under 95% RH |
|---|---|---|
| Form III | 0.8% | 2.4% |

Hygroscopicity criteria applied in this example refer to the standard in European pharmacopoeia:
 deliquescent: sufficient water is absorbed to form a liquid,
 very hygroscopic: increase in mass is equal to or greater than 15 percent,
 hygroscopic: increase in mass is less than 15 percent and equal to or greater than 2 percent,
 slightly hygroscopic: increase in mass is less than 2 percent and equal to or greater than 0.2 percent.

Example 7. Preparation of Form α of Lesinurad Sodium Salt

In 1.0 mL of water was dissolved 200 mg of amorphous lesinurad sodium salt. The clear solution was stirred under ambient conditions for 24 hours. The precipitate was isolated by centrifugation and crystalline Form α was obtained, which was analyzed by XRPD, DSC, and TGA. The XRPD data of the lesinurad sodium salt Form α obtained in this example are listed in Table 7.

The XRPD pattern and DSC thermogram of the Form α obtained from this example are displayed in FIGS. 12 and 13, respectively. The thermal gravimetric analysis of the sample showed weight loss of about 13.1% when heated to 50.0° C., and a total weight loss of about 22.7% when heated to 110.0° C., indicating that the sample was likely a solvate (hepta-hydrate).

Figure 14:
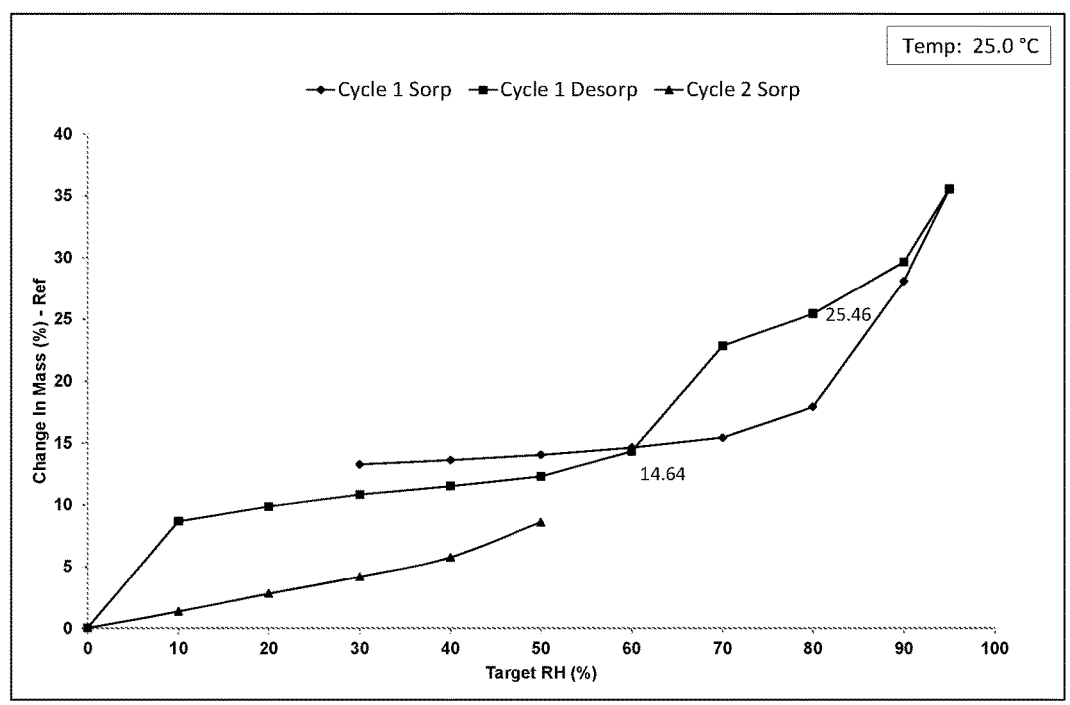
FIG. 14 shows an illustrative dynamic vapor sorption (DVS) isothermal plot of Form α of lesinurad sodium salt.

DVS isothermal plot shows in FIG. 14.

TABLE 7

| 2 theta | d spacing | intensity % |
|---|---|---|
| 6.80 | 12.99 | 8.06 |
| 7.60 | 11.64 | 22.92 |
| 8.60 | 10.29 | 5.66 |
| 10.51 | 8.41 | 2.68 |
| 13.80 | 6.42 | 7.98 |
| 15.36 | 5.77 | 0.75 |
| 17.55 | 5.05 | 23.95 |
| 21.15 | 4.20 | 13.45 |
| 22.32 | 3.98 | 4.18 |
| 22.79 | 3.90 | 100.00 |
| 23.08 | 3.85 | 7.29 |
| 25.08 | 3.55 | 51.65 |
| 25.62 | 3.48 | 13.38 |
| 26.27 | 3.39 | 6.17 |
| 27.10 | 3.29 | 11.17 |
| 27.62 | 3.23 | 5.21 |
| 27.89 | 3.20 | 21.14 |
| 28.77 | 3.10 | 12.48 |
| 29.38 | 3.04 | 1.80 |
| 29.91 | 2.99 | 7.98 |
| 30.20 | 2.96 | 3.27 |
| 30.56 | 2.92 | 3.04 |
| 31.15 | 2.87 | 7.59 |
| 31.47 | 2.84 | 4.64 |
| 32.84 | 2.73 | 3.55 |
| 33.53 | 2.67 | 1.47 |
| 34.55 | 2.60 | 3.64 |
| 35.19 | 2.55 | 2.80 |
| 36.10 | 2.49 | 1.72 |
| 37.36 | 2.41 | 1.98 |
| 38.41 | 2.34 | 2.34 |
| 6.80 | 12.99 | 8.06 |
| 7.60 | 11.64 | 22.92 |
| 8.60 | 10.29 | 5.66 |
| 10.51 | 8.41 | 2.68 |
| 13.80 | 6.42 | 7.98 |
| 15.36 | 5.77 | 0.75 |
| 17.55 | 5.05 | 23.95 |
| 21.15 | 4.20 | 13.45 |
| 22.32 | 3.98 | 4.18 |
| 22.79 | 3.90 | 100.00 |
| 23.08 | 3.85 | 7.29 |
| 25.08 | 3.55 | 51.65 |
| 25.62 | 3.48 | 13.38 |
| 26.27 | 3.39 | 6.17 |
| 27.10 | 3.29 | 11.17 |
| 27.62 | 3.23 | 5.21 |
| 27.89 | 3.20 | 21.14 |
| 28.77 | 3.10 | 12.48 |
| 29.38 | 3.04 | 1.80 |

TABLE 7-continued

| 2 theta | d spacing | intensity % |
|---|---|---|
| 29.91 | 2.99 | 7.98 |
| 30.20 | 2.96 | 3.27 |
| 30.56 | 2.92 | 3.04 |
| 31.15 | 2.87 | 7.59 |
| 31.47 | 2.84 | 4.64 |
| 32.84 | 2.73 | 3.55 |
| 33.53 | 2.67 | 1.47 |
| 34.55 | 2.60 | 3.64 |
| 35.19 | 2.55 | 2.80 |
| 36.10 | 2.49 | 1.72 |
| 37.36 | 2.41 | 1.98 |
| 38.41 | 2.34 | 2.34 |

Example 8. Preparation of Form β of Lesinurad Sodium Salt

In 0.5 mL of ethyl acetate/water (976:24, v/v) was dissolved 50 mg of amorphous lesinurad sodium salt. The clear solution was stirred under ambient conditions for 48 hours. The precipitate was isolated by centrifugation and Form β was obtained, which was analyzed by XRPD, DSC, and TGA. The XRPD data of the lesinurad sodium salt Form β obtained in this example are listed in Table 8.

The XRPD pattern and DSC thermogram of lesinurad sodium salt Form β obtained from this example are displayed in FIGS. 15 and 16, respectively. The thermal gravimetric analysis of the sample showed weight loss of about 3.6% when heated to 42.5° C., and a total weight loss of about 14.6% when heated to 100.0° C., indicating that the sample was likely a solvate (tetra-hydrate).

TABLE 8

| 2 theta | d spacing | intensity % |
|---|---|---|
| 4.58 | 19.28 | 37.67 |
| 9.19 | 9.62 | 100.00 |
| 10.27 | 8.61 | 27.38 |
| 12.87 | 6.88 | 32.49 |
| 13.82 | 6.41 | 19.81 |
| 14.73 | 6.01 | 19.91 |
| 17.76 | 4.99 | 26.56 |
| 18.45 | 4.81 | 44.37 |
| 19.93 | 4.46 | 36.12 |
| 21.84 | 4.07 | 29.53 |
| 22.52 | 3.95 | 25.66 |
| 23.13 | 3.84 | 44.57 |
| 23.63 | 3.77 | 37.39 |
| 25.20 | 3.53 | 30.66 |
| 26.01 | 3.43 | 25.46 |
| 26.74 | 3.33 | 26.26 |
| 27.87 | 3.20 | 24.10 |
| 28.48 | 3.13 | 26.82 |
| 28.89 | 3.09 | 22.46 |
| 29.94 | 2.98 | 31.91 |
| 31.34 | 2.85 | 10.72 |
| 35.46 | 2.53 | 14.25 |
| 36.25 | 2.48 | 10.11 |
| 38.90 | 2.32 | 10.29 |

Example 9. Preparation of Form γ of Lesinurad Sodium Salt

In 2.0 mL of ethyl acetate was dissolved 3.8 mg of amorphous lesinurad sodium salt. The clear solution was stirred under ambient conditions until precipitation. The precipitate was isolated by centrifugation and Form γ was obtained, which was analyzed by XRPD, DSC, and TGA. The XRPD data of the lesinurad sodium salt Form γ obtained in this example are listed in Table 9.

The XRPD pattern and DSC thermogram of lesinurad sodium salt Form γ obtained from this example are displayed in FIGS. 17 and 18, respectively. The thermal gravimetric analysis of the sample showed weight loss of about 6.0% when heated to 36.1° C., and a total weight loss of about 16.5% when heated to 100.0° C., indicating that the sample was likely a solvate (hydrate).

TABLE 9

| 2 theta | d spacing | intensity % |
|---|---|---|
| 4.69 | 18.84 | 83.23 |
| 7.32 | 12.07 | 58.33 |
| 9.31 | 9.50 | 77.56 |
| 10.37 | 8.53 | 100 |
| 12.60 | 7.02 | 33.24 |
| 12.97 | 6.83 | 76.17 |
| 13.78 | 6.43 | 16.87 |
| 14.82 | 5.98 | 24.33 |
| 15.64 | 5.67 | 24.54 |
| 16.12 | 5.50 | 26.08 |
| 17.82 | 4.98 | 46.87 |
| 18.19 | 4.88 | 25.02 |
| 18.61 | 4.77 | 19.16 |
| 20.05 | 4.43 | 28.19 |
| 20.72 | 4.29 | 6.26 |
| 21.94 | 4.05 | 40.5 |
| 22.52 | 3.95 | 39.13 |
| 22.77 | 3.91 | 33.29 |
| 23.71 | 3.75 | 65.7 |
| 24.34 | 3.66 | 19.35 |
| 25.26 | 3.53 | 58.83 |
| 26.05 | 3.42 | 33.47 |
| 26.57 | 3.35 | 11.78 |
| 27.95 | 3.19 | 14.21 |
| 28.60 | 3.12 | 34.66 |
| 29.01 | 3.08 | 31.88 |
| 29.98 | 2.98 | 24.23 |
| 30.57 | 2.92 | 19.26 |
| 31.32 | 2.86 | 20.55 |
| 32.57 | 2.75 | 11.2 |
| 35.50 | 2.53 | 12.57 |
| 38.77 | 2.32 | 4.68 |

Example 10. Preparation of Form δ of Lesinurad Sodium Salt

To 0.15 mL of 2-methyl terahydrofuran/water (19:1, v/v) was added 18.8 mg of lesinurad sodium salt amorphous. The mixture was heated to 50° C., and cooled to 5° C. at the rate of 0.05° C./min, then equilibrated at 5° C. for 32 hours. The precipitate was isolated by centrifugation and Form δ was obtained, which was analyzed by XRPD. The XRPD data of the lesinurad sodium salt Form δ obtained in this example are listed in Table 10.

The XRPD pattern of lesinurad sodium salt Form δ obtained from this example is displayed in FIG. 19.

TABLE 10

| 2 theta | d spacing | intensity % |
|---|---|---|
| 4.50 | 19.63 | 18.23 |
| 9.04 | 9.78 | 100 |
| 13.65 | 6.49 | 9.24 |
| 18.23 | 4.87 | 49.17 |
| 22.86 | 3.89 | 31.57 |
| 27.51 | 3.24 | 10.07 |
| 29.45 | 3.03 | 4.08 |

Example 11. Inter-Conversion Relationship Between Form α of Lesinurad Sodium Salt and its Form A (WO2011085009A2)

Figure 20:
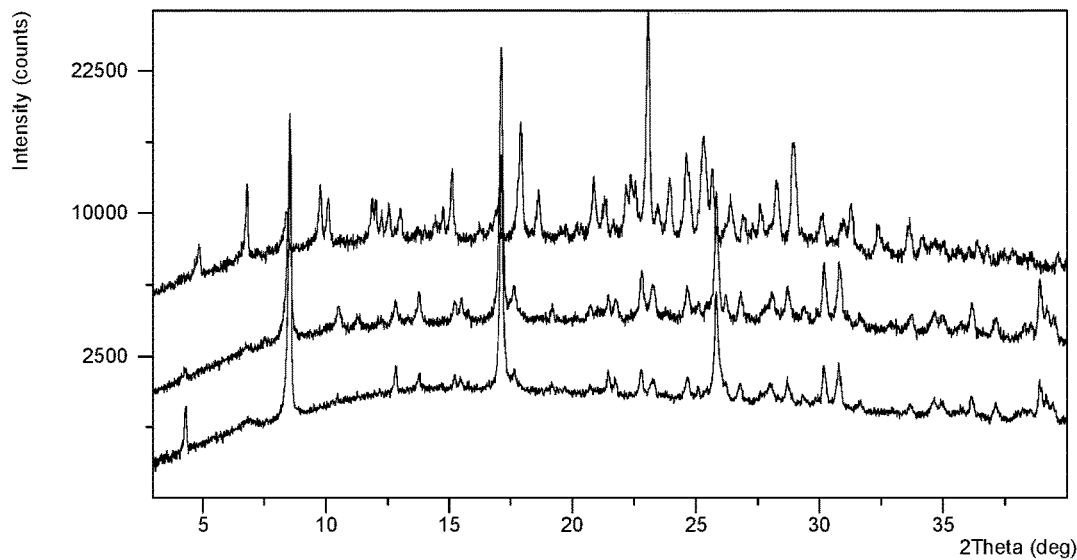
FIG. 20 shows inter-conversion relationship between Form α of lesinurad sodium salt and its Form A reported literature (WO2011085009A2) (top pattern: XRPD of Form A; middle pattern: XRPD of Form α; bottom pattern: XRPD after Form A was stirred in water, which changed to Form α).

Form A converts to Form α after stirring in water at 500 rpm for 24 hours under ambient conditions. Inter-conversion relationship between lesinurad sodium salt Form α and Form A (WO2011085009A2) is shown in FIG. 20 (a: XRPD pattern of Form A; b: XRPD pattern of Form α; c: XRPD pattern after Form A was stirred in water, which changed to Form α), suggesting that Form α is more stable in comparison to Form A in water under ambient conditions.

Figure 21:
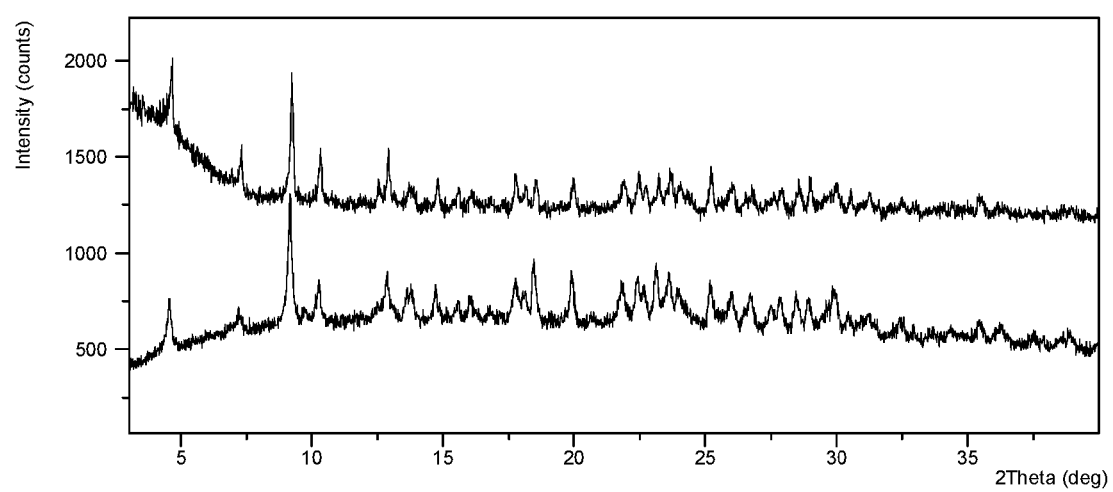
FIG. 21 shows comparison of the XRPD pattern of Form β of lesinurad sodium salt before storage (top pattern) and after being stored under room temperature for 12 months (bottom pattern).

Example 12. Stability Assessment of Lesinurad Sodium Salt Form β Under Stress Conditions A sample of the lesinurad sodium salt Form β was stored under room temperature for 12 months. The solid sample was analyzed by XRPD. The XRPD patterns of the Form β sample before storage (top pattern) and after being stored under room temperature for 12 months (bottom pattern) are displayed in FIG. 21. The results of stability assessment tabulated in Table 11 suggest that Form β is stable under the stress conditions.

TABLE 11

| Initial form | Conditions | Storage time | Final form |
| --- | --- | --- | --- |
| lesinurad sodium salt Form β (top pattern in FIG. 22) | Room temperature | 12 months | lesinurad sodium salt Form β (bottom pattern in FIG. 22) |

The foregoing examples and description of the preferred embodiments should be taken as illustrating, rather than as limiting, the present invention as defined by the claims. As will be readily appreciated by a person skilled in the art, numerous variations and combinations of the features set forth above can be utilized without departing from the present invention as set forth in the claims. All such variations are intended to be included within the scope of the following claims. All references cited herein are incorporated by reference in their entireties.

What is claimed is:

1. A crystalline form of lesinurad, designated as Form III, having an X-ray powder diffraction pattern comprising the following 2θ values measured using CuKα radiation: 11.9°±0.2°, 15.3°±0.2°, 20.8°±0.2°, and 23.8°±0.2°,
    wherein Form III is stable upon storage for 14 days at 40° C./75% relative humidity.

2. The crystalline Form III of claim 1, wherein the X-ray powder diffraction pattern further comprises the following 2θ values measured using CuKα radiation: 17.8°±0.2°, 27.2°±0.2°, and 7.9°±0.2°.

3. The crystalline Form III of claim 1, wherein the X-ray powder diffraction pattern further comprises the following 2θ values measured using CuKα radiation: 17.4°±0.2°, and 22.4°±0.2°.

4. The crystalline form of lesinurad, designated as Form III of claim 1, having the following 2θ values ±0.2°:
    7.95, 9.52, 10.04, 11.93, 12.94, 13.53, 14.46, 15.34, 15.94, 17.36, 17.77, 18.82, 19.55, 20.85, 22.44, 23.76, 24.04, 25.43, 26.21, 27.24, 28.10, 32.42, and 34.72.

5. The crystalline Form III of claim 1, which is in the anhydrous state.

\* \* \* \* \*